United States Patent [19]

Michelson

[11] Patent Number: 4,985,019
[45] Date of Patent: Jan. 15, 1991

[54] X-RAY MARKER

[76] Inventor: Gary K. Michelson, 438 Sherman Canal, Venice, Calif. 90291

[21] Appl. No.: 167,168

[22] Filed: Mar. 11, 1988

[51] Int. Cl.⁵ ............................................. A61F 13/02
[52] U.S. Cl. ........................... 604/180; 128/DIG. 26; 378/164
[58] Field of Search ............. 604/116, 174, 180; 378/204, 205, 208, 162–165; 128/DIG. 26

[56] References Cited

U.S. PATENT DOCUMENTS

| | | | |
|---|---|---|---|
| 2,586,940 | 2/1952 | Graham | 128/DIG. 26 |
| 2,606,555 | 8/1952 | Solomon | 128/DIG. 26 |
| 3,016,899 | 1/1962 | Stenvall | 604/116 |
| 3,288,137 | 11/1966 | Lund | 128/DIG. 26 |
| 3,547,121 | 12/1970 | Cherry | 604/116 |
| 3,770,956 | 11/1973 | Johnson | 378/164 |
| 3,848,136 | 11/1974 | Seldin | 378/164 |
| 3,920,001 | 11/1975 | Edwards | 604/116 |
| 4,516,968 | 5/1985 | Marshall et al. | 128/DIG. 26 |
| 4,543,091 | 9/1985 | Froning et al. | 604/116 |
| 4,579,120 | 4/1986 | Mac Gregor | 604/180 |
| 4,675,006 | 6/1987 | Hrushesky | 604/180 |
| 4,733,661 | 3/1988 | Palestrant | 604/116 |
| 4,759,045 | 7/1988 | Lasky | 378/162 |
| 4,792,330 | 12/1988 | Lazarus et al. | 128/DIG. 26 |
| 4,915,694 | 4/1990 | Yamamoto et al. | 604/180 |

FOREIGN PATENT DOCUMENTS 699253 11/1953 United Kingdom ................. 604/175

*Primary Examiner*—Stephen C. Pellegrino
*Assistant Examiner*—Ralph Lewis
*Attorney, Agent, or Firm*—Lewis Anten

[57] ABSTRACT

An adhesively applied marker for use in determining the location of where a spinal marker needle is to be placed is disclosed. The markers have a radiopaque grid pattern and other indicia on the surface of the marker so that when adhesively applied to the patient, they will clearly show the location of the markers in relationship to the body of the patient. A central opening for a marker needle is also provided. The discs are made in various sizes, for different applications.

8 Claims, 1 Drawing Sheet

X-RAY MARKER

BACKGROUND

Various adhesively applied radiographic opaque products have been used for the purpose of determining a location of a point on the body. For example, there are nipple markers that have a BB-like center portion for placement on the nipples before the taking of an X-ray. The location of the nipples may then be observed directly on the X-ray. Such devices, however, are adhesively applied to the patient. Such devices do not require that they be applied, removed and then reapplied to locate a particular point of the body. Also, such devices are used solely for the purpose of locating the external position of the marker. Also, the presently available markers do not assist in the actual placement of a needle into a patient.

SUMMARY OF THE INVENTION

In the present invention, an adhesively applied marker disc has a grid pattern and other indicia, such as score marks and arrows for easily determining the location and orientation of the marker in relation to the body or any specific part. The grid pattern and other indicia is radiographically opaque. The adhesive marker has a partially removable adhesive backing so that the marker may be temporarily applied, an X-ray taken and if the marker is not properly positioned, it may then be easily removed and then reapplied to the patient and the process repeated.

The marker has a central opening with a raised ridge portion for guiding the placement of a needle through the opening in the marker.

DETAILED DESCRIPTION OF THE DRAWINGS

Figure 1:
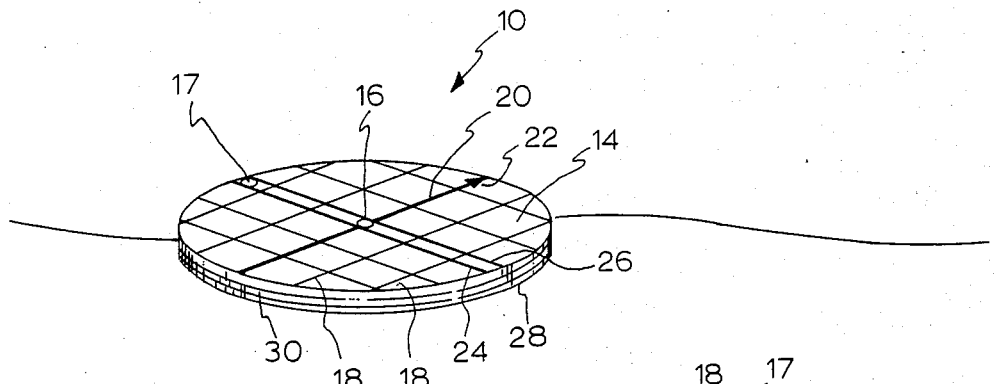
FIG. 1 is a perspective view of the present invention.
Figure 2:
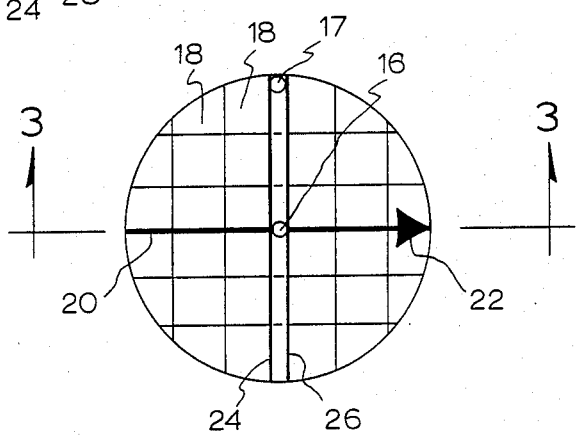
FIG. 2 is a top view of the present invention.
Figure 3:
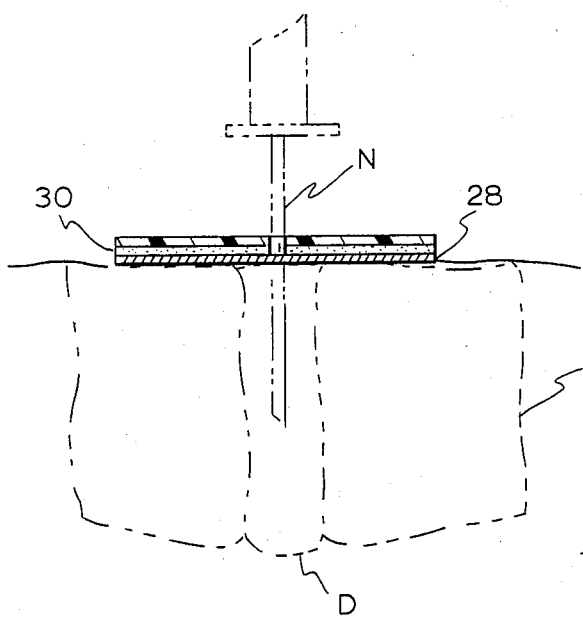
FIG. 3 is a side view of the present invention.

Referring to FIGS. 1-3, an adhesive marker 10 has a top surface 14. An opening 16, slightly larger than the size of a desired needle to be used, is located at the center of the marker.

A grid pattern 18 of a radiopaque material is located on the top surface 14 of the marker 10. Main line 20 terminates in a direction arrow 22 also of radiopaque material and passes through the center of opening 16 of marker 10. Perpendicular to the main line 20 are a pair of wide parallel lines 24 and 26 which are placed on the tangent of the central opening 16. A second marking indicia 17 in the form of a spot may also be provided in the top surface 14 of the marker 10. An adhesive layer 30 is applied to the bottom surface of the marker 10. A removable backing sheet 28 is applied to the adhesive layer 30.

The devise is used as follows: The removable backing sheet 28 is removed and the marker 10 is lightly placed on the patient in the approximate location where the needle is thought to be inserted, for example, at the location of a disc D between cartilage C. The X-ray would then be taken and if the opening 16 of the marker 10 is not in the desired position, the marker 10 would be lifted and moved to the new position. The spaces between the grid pattern 18 are a fixed amount apart, for example, 2 or 3 millimeters, so that by observing the main line 20 and arrow 22 the orientation of the marker on the patient can be determined. Once the central opening 16 of the marker 10 is determined from the X-ray to be in the proper location, the marker 10 is pressed down and the needle N may then be inserted through the opening 16.

Figure 4:
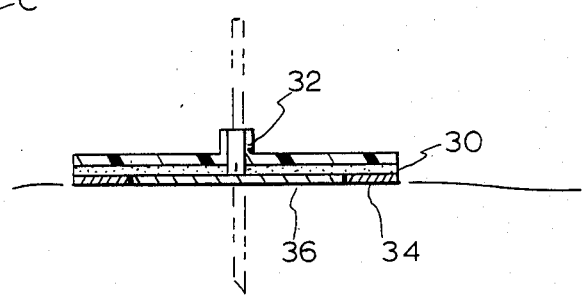
FIG. 4 is an alternative view of the present invention.

Referring to FIG. 4, an alternative embodiment of the present invention is disclosed. The top surface 14 of the marker 10 has a central ridge projection 32 surrounding the opening 16 for assisting in aligning the needle N in a perpendicular orientation. The projection 32 is approximately ¼ inch above the top surface 14 of the marker 10, although it could be higher, depending on the caliber of the needle to be used.

On the lower surface of the adhesive 30 is an inner backing 36 and a smaller outer backing 34. The smaller outer backing 34 portion is capable of being removed to expose a small portion of the adhesive 30 so that the marker 10 may be applied and then removed again. Once then proper location of the marker is determined, then the larger inner backing 36 is removed and the marker 10 pressed down, fixedly applying the marker 10 to the patient. The marker 10 does not have to be completely removed in order to remove the inner backing 36, so the orientation of the marker 10 is not compromised while the marker 10 is being applied to the final location.

What is claimed is:

1. A radiographic marker comprising:
   first substantially rigid disc member having at least a portion thereof radio opaque, said radiographic opaque portion of said disc in the form of a grid, said member having a top surface and a bottom surface and a circular opening in said disc, the central axis of said opening substantially perpendicular to the plane of said disc and adapted to permit the tip of a needle to pass therethrough and be supported by the walls of said opening and adhesive applied to said bottom surface for applying said marker to the body of a patient.

2. The apparatus of claim 1 in which said circular opening has a raised ridge portion surrounding at least a portion of said opening.

3. The marker of claim 1 in which said marker has a removable backing covering said adhesive.

4. The marker of claim 3 in which said removable backing has a first and a second portion.

5. The apparatus of claim 3 in which said removable backing includes more than one segment.

6. The X-ray member of claim 1 in which portions of said disc are not radio opaque.

7. The X-ray marker of claim 1 in which said opening in said disc has a raised ridge surrounding at least a portion of said opening on the top surface.

8. A radiographic marker comprising:
   first substantially rigid disc member having at least a portion thereof radio opaque, said member having a top surface and a bottom surface and a circular opening in said disc, the central axis of said opening substantially perpendicular to the plane of said disc and adapted to permit the tip of a needle to pass therethrough and be supported by the walls of said opening and adhesive applied to said bottom surface for applying said marker to the body of a patient, said marker having a first radiographical opaque marking thereon and a second radiographic opaque portion having a non symmetrical orientation for displaying the orientation of said marker.

* * * * *